United States Patent [19]

Kurahashi et al.

[11] Patent Number: 4,708,953

[45] Date of Patent: Nov. 24, 1987

[54] SALICYLAMIDE DERIVATIVES

[75] Inventors: Yoshio Kurahashi, Hachioji; Kozo Shiokawa, Kawasaki; Toshio Goto, Machida; Shinzo Kagabu, Hachioji; Noboru Matsumoto, Hachioji; Koichi Moriya, Hachioji, all of Japan

[73] Assignee: Nihon Tokushu Noyaku Seizo K.K., Tokyo, Japan

[21] Appl. No.: 774,272

[22] Filed: Sep. 10, 1985

[30] Foreign Application Priority Data

Sep. 13, 1984 [JP] Japan .................. 59-190605

[51] Int. Cl.$^4$ .................. C07C 103/78; A01N 37/40
[52] U.S. Cl. .................. 514/166; 564/177; 514/622
[58] Field of Search ............. 514/166, 622; 564/177

[56] References Cited

U.S. PATENT DOCUMENTS 2,728,660 12/1955 Salminen .................. 564/177 X
4,200,632 4/1980 Nakagawa et al. .......... 564/177 X

FOREIGN PATENT DOCUMENTS 56-35662 8/1981 Japan .
139351 8/1984 Japan .
204161 11/1984 Japan .................. 564/177

Primary Examiner—Charles F. Warren
Assistant Examiner—Carolyn S. Greason
Attorney, Agent, or Firm—Sprung Horn Kramer & Woods

[57] ABSTRACT

Salicylamide derivatives of the formula

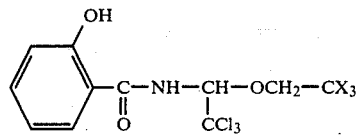

in which

X is a halogen atom, are active against fungi, especially those which result in clubroot of cruciferous plants.

7 Claims, No Drawings

SALICYLAMIDE DERIVATIVES

The present invention relates to novel salicylamide derivatives, to a process for their preparation and to their use as fungicides, particularly against diseases of subterranean portions of plants.

It has already been disclosed that a certain salicylamide derivative is useful as a soil-fungicide (see Japanese Patent Publication No. 35662/1981).

There have now been found novel salicylamide derivatives of the formula (I)

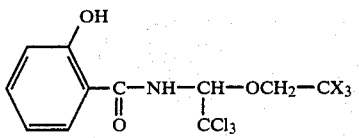

wherein X represents halogen.

Salicylamide derivatives of the formula (I) are obtained when the compounds of the formula (II)

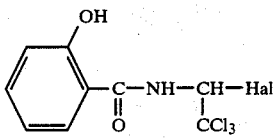

wherein Hal represents a halogen atom,
are reacted with compounds of the formula (III)

     (III)

wherein X represents a halogen atom,
if appropriate, in the presence of acid acceptors and inert solvents.

The novel salicylamide derivatives exhibit powerful fungicidal properties, particularly for plant disease in soil.

Surprisingly, the salicylamide derivatives according to the invention exhibit a substantially greater fungicidal action against diseases of subterranean portions of plants than those known from the aforementioned prior art and, in particular, the compounds of the formula (I) are extremely active against clubroot of cruciferous plants.

Among the salicylamide derivatives according to the invention of the formula (I), preferred compounds are those in which X represents chlorine, fluorine or bromine.

Very particularly preferred salicylamide derivatives of the formula (I) are those in which X represents chlorine or fluorine.

Specifically, the following compounds may be mentioned:
N-[2,2,2-trichloro-1-(2,2,2-trichloroethoxy)ethyl]-salicylamide,
N-[2,2,2-trichloro-1-(2,2,2-trifluoroethoxy)ethyl]-salicylamide.

If, for example, N-(1,2,2,2-tetrachloroethyl)-salicylamide and 2,2,2-trifluoroethanol are used as starting materials, the course of the reaction can be represented by the following equation:

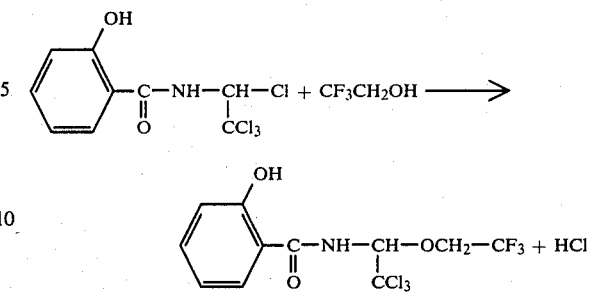

The formula (II) provides a general definition of the compounds required as starting materials in the above reaction variant according to the invention.

In formula (II), Hal represents a halogen atom, preferably chlorine or bromine.

The compounds of the formula (II) usable according to the invention are already known (see Japanese Patent Publication No. 35662/1981) and can be easily produced by reacting salicylamide with chloral, and then reacting the product with a halogenating agent.

As examples there may be mentioned:
N-(1,2,2,2-tetrachloroethyl) salicylamide,
N-(1-bromo-2,2,2-trichloroethyl)salicylamide.

The formula (III) provides a general definition of the compounds required as starting materials in the above reaction variant according to the invention.

In formula (III), X preferably has the meanings already given above.

The compounds (III) usable according to the invention are already known.

As examples there may be mentioned:
2,2,2-trifluoroethanol,
2,2,2-trichloroethanol,
2,2,2-tribromoethanol.

Suitable diluents are all inert organic solvents.

These preferentially include aliphatic, alicyclic and aromatic hydrocarbons (which may optionally be chlorinated), such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; esters such as ethyl acetate and amyl acetate; acid amides such as dimethylformamide and dimethylacetamide; sulfones and sulfoxides such as dimethyl sulfoxide and sulfolane; and bases such as pyridine.

The reaction in accordance with this invention can be carried out in the presence of acid acceptors. Examples of the acid binder include the hydroxides, carbonates, bicarbonates and alcoholates of alkali metals and tertiary amines such as triethylamine, diethylaniline and pyridine, which are generally used.

The above process can be carried out over a wide temperature range. Generally, it can be carried out at a temperature between about −20° C. and the boiling point of the mixture, desirably between about 0° C. and about 100° C. Desirably, the reaction is carried out under ambient pressure, but it is also possible to operate under elevated or reduced pressures.

The active substances according to the invention exhibit powerful preventing effects against plant diseases in soil. They can therefore be used as fungicides (preventing agents) against diseases of subterranean portions of plants.

Specifically, the active substances show extremely excellent preventing effects against clubroot (*Plasmodiophora brassicae*) of cruciferous plants.

The compounds of this invention also show a superior efficacy against *Aphanomyces cochlioides* disease, a kind of damping-off of seedlings, and moreover have excellent bactericidal and fungicidal activity against microorganisms to be controlled broadly by industrial fungicides, for example *Aerobacter aerogenes, Staphylococcus aureus, Bacillus subtilis, Escherichia coli, Aspergillus niger, Trichoderma viride*, Penicillium sp., Rhizopus sp. and Fusarium sp.

As fungicides against plant disease in soil, for example, preventing agents against clubroot of cruciferous plants, the compounds of the formula (I) according to the invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agriculturally acceptable adjuvants as referred to herein include, for example, diluents (solvents, extenders, carriers), surface-active agents (solubilizing agents, emulsifiers, dispersing agents, wetting agents), stabilizers, stickers, aerosol propellants and synergists.

The solvents may be water and organic solvents. Examples of the organic solvents are hydrocarbons [such as n-hexane, petroleum ether, petroleum fractions (e.g., paraffin waxes, kerosene, light oils, middle oils and heavy oils), benzene, toluene, and xylene], halogenated hydrocarbons (such as methylene chloride, carbon tetrachloride, ethylene chloride, ethylene dibromide, chlorobenzene and chloroform), alcohols (such as methanol, ethanol, propanol and ethylene glycol), ethers (such as diethyl ether, ethylene oxide and dioxane), alcohol ethers (such as ethylene glycol monomethyl ether), ketones (such as acetone and isophorone), esters (such as ethyl acetate and amyl acetate), amides (such as·dimethylformamide and dimethylacetamide) and sulfoxides (such as dimethylsulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (such as pyrophyllite talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfonic acid esters (such as sodium laurylsulfate), arylsulfonic acids (such as alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condention products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers stickers (such as agricultural soaps, casein lime, sodium alginate, polyvinyl alcohol, vinyl acetate-type adhesives and acrylic adhesives); effect-prolonging agents; dispersion stabilizers [such as casein, tragacanth, carboxymethyl cellulose (CMC), and polyvinyl alcohol (PVA)]; and synergists.

The compounds of this invention can be formulated into various forms by methods generally practiced in the production of agricultural chemicals. Illustrative of such forms are emulsifiable concentrates, wettable powders, soluble powders, suspensions, dusts, granules, pulverulent preparations, and capsules. Dusts, granules and pulverulent preparations are preferred.

The clubroot controlling agent of this invention for cruciferous plants may contain about 0.1 to about 95% by weight, preferably about 0.5 to about 90% by weight, of the aforesaid active ingredient.

In actual use, the suitable amount of the active compound in the aforesaid various formulations and ready-to-use preparations is generally about 0.0001 to about 20% by weight, preferably about 0.005 to about 10% by weight.

The content of the active ingredient can be properly varied depending upon the type of the formulation, the method, purpose, time and locus of its application, and the state of occurrence of the disease.

If required, the compounds of this invention may be used in combination with other agricultural chemicals, for example insecticides, other fungicides, miticides, nematocides, antiviral agents, herbicides, plant growth regulators and attractants [such as organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds], and/or fertilizers.

Various formulations and ready-to-use preparations containing the aforesaid active ingredient of the invention can be applied by various methods generally practiced in the field of agricultural chemical application, for example soil application (mixing, sprinkling, vaporing and pouring etc.). It can also be used by the so-called ultralow volume spraying method. According to this method, the active ingredient may be included in an amount of 100%.

The rate of application per unit area is, for example, about 0.5 to about 30 kg, preferably about 1 to about 20 kg, per hectare. In special cases, however, it may, and sometimes should, be outside the specified range.

According to this invention, there can be provided a clubroot controlling composition for cruciferous plants comprising the compound of general formula (I) as an active ingredient and a diluent (a solvent and/or an extender and/or a carrier) and/or a surface-active agent, and if further required, a stabilizer, a sticker, and a synergist.

This invention also provides a method for controlling clubroot of cruciferous plants, which comprises applying to a clubroot fungus and/or the locus of its occurrence the compound of general formula (I) either singly or in admixture with a diluent (a solvent and/or an extender and/or a carrier) and/or a surface-active agent and if further required, a stabilizer, a sticker and a synergist.

The following examples illustrate the present invention specifically. It should be noted however that the invention is not limited to these specific examples alone.

PREPARATION EXAMPLES

Example 1

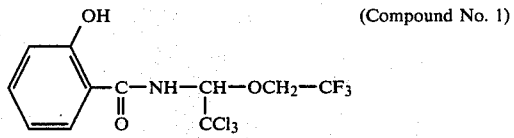
(Compound No. 1)

A solution of N-(1,2,2,2-tetrachloroethyl) salicylamide (30 g) in toluene (100 ml) is added dropwise at less than 10° C. to a solution of 2,2,2-trifluoroethanol (10 g) and pyridine (18.6 g) in toluene (150 ml). After the addition, the mixture is stirred at room temperature for a while, and the contents are washed with water and a 1% aqueous solution of sodium hydrogen carbonate. The toluene layer is dehydrated, and the toluene is evaporated under reduced pressure to give the desired N-[2,2,2,-trichloro-1-(2,2,2,-trifluoroethoxy) ethyl]-salicylamide (26 g) represented by the foregoing formula as a colorless viscous mass. This compound gradually solidifies and shows a melting point of 78° to 82° C.

Example 2

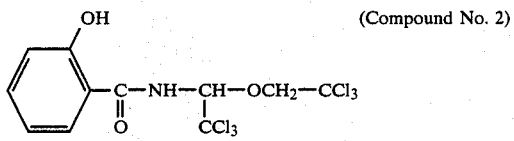
(Compound No. 2)

A solution composed of 2,2,2-trichloroethanol (30 g), N-(1,2,2,2-tetrachloroethyl) salicylamide (30 g) and toluene (200 ml) is refluxed until the generation of hydrogen chloride ceases (for about 5 to 8 hours). The reaction mixture is cooled to room temperature. The toluene layer is washed with water and dehydrated, and toluene is evaporated under reduced pressure to give the desired N-8 2,2,2-trichloro-1-(2,2,2-trichloroethoxy)-ethyl]salicylamide (37 g) represented by the foregoing formula as colorless crystals. mp. 111°-114° C.

In accordance with the same method as above, 2,2,2-tribromoethanol and N-(1,2,2,2-tetrachloroethyl)-salicylamide are reacted to synthesize N-[2,2,2-trichloro-1-(2,2,2-tribromoethoxy)ethyl]salicylamide (compound No. 3 of the invention).

Use examples

The known comparison compounds are identified as follows:

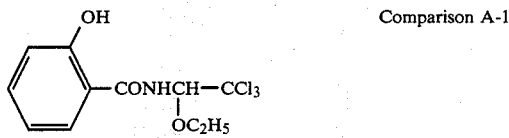
Comparison A-1

(the compound described in the specification of Japanese Patent Publication No. 35662/1981).

PCNB: Pentachloronitrobenzene (20% dust)

Example 3

Test for control of clubroot of "komatsuna" (a variety of Chinese cabbage):

Testing method

Unglazed pots having a diameter of 21 cm are filled with soil infected by the clubroot fungus (*Plasmodiophora brassicae*), and a dust of the compound of this invention prepared as in Example 5 hereinbelow is mixed uniformly with the soil to a predetermined concentration.

Seeds of komatsuna (variety: Misugi) are sown on the soil at a rate of 20 per pot. The pots are maintained in an air-conditioned greenhouse at 20° C. for 4 weeks. Then, the plants are dug up, and the condition of the disease is evaluated by the following standards. The disease index and the rate of diseased plants are calculated.

Degree of disease

3: $L_1$, the number of plants whose roots become markedly enlarged by the occurrence of clubroot 2: $L_2$, the number of plants in which the occurrence of clubroot is observed but limited to the main roots 1: $L_3$, the number of plants in which the occurrence of clubroot is slightly observed 0: $L_4$, the number of sound plants $$\text{Disease index} = \frac{3 \times L_1 + 2 \times L_2 + 1 \times L_3}{3 \times (L_1 + L_2 + L_3 + L_4)} \times 100$$

$$\text{Rate of diseased plants} = \frac{L_1 + L_2 + L_3}{L_1 + L_2 + L_3 + L_4} \times 100$$

The results are shown in Table 1.

TABLE 1

| Compound No. | Amount of the active ingredient (kg/ha) | Disease index (%) | Rate of diseased plants (%) | Phytotoxicity |
|---|---|---|---|---|
| 1 | 20 | 0 | 0 | None |
|   | 10 | 0 | 0 | " |
|   | 5 | 0 | 0 | " |
| 2 | 20 | 0 | 0 | None |
|   | 10 | 0 | 0 | " |
|   | 5 | 1.7 | 5 | " |
| Comparison |  |  |  |  |
| A-1 | 20 | 33.3 | 45 | None |
|   | 10 | 80 | 85 | " |
|   | 5 | 81.7 | 95 | " |
| PCNB (commercial) | 60 | 58.3 | 75 | None |
| Non-treated | — | 95 | 100 | — |

Example 4

Two parts of compound No. 1 of the invention and 98 parts of powdery clay are pulverized and mixed to form a dust. It is scattered onto, and mixed with, the soil where the occurrence of clubroot is anticipated.

Example 5

Compound No. 2 of the invention (1.5 parts), 0.5 part of isopropyl hydrogen phosphate (PAP) and 98 parts of powdery clay are pulverized and mixed to form a dust. It is scattered onto, and mixed with, the soil where clubroot occurs or its occurrence is anticipated.

Example 6

Water (25 parts) is added to a mixture consisting of 10 parts of compound No. 1 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered onto, and mixed with, the soil where clubroot occurs or its occurrence is anticipated.

Example 7

Ninety-five parts of clay mineral particles having a particle size distribution between 0.2 and 2 mm are put in a rotary mixer, and with rotation, 5 parts of compound No. 2 of the invention dissolved in an organic solvent is sprayed onto the particles to wet them uniformly to form granules. They are then dried at 40° to 50° C. The granules are scattered onto, and mixed with, the soil where clubroot occurs or its occurrence is anticipated.

It will be understood that the specification and examples are illustrative but not limitative of the present invention and that other embodiments within the spirit and scope of the invention will suggest themselves to those skilled in the art.

We claim:

1. A salicylamide of the formula

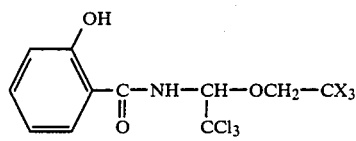

in which
X is a halogen atom.

2. A compound according to claim 1, in which X is chlorine, fluorine or bromine.

3. A compound according to claim 1, in which X is chlorine or fluorine.

4. A compound according to claim 1, wherein such compound is N-[2,2,2-trichloro-1-(2,2,2-trichloroethoxy)-ethyl]-salicylamide of the formula

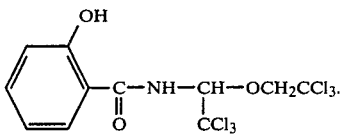

5. A compound according to claim 1, wherein such compound is N-[2,2,2-trichloro-1-(2,2,2-trifluoroethoxy)-ethyl]-salicylamide of the formula

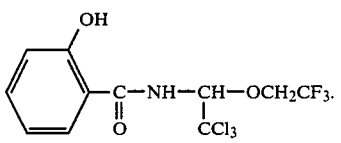

6. A compound according to claim 1, wherein such compound is N-[2,2,2-trichloro-1-(2,2,2-tribromoethoxy)-ethyl]-salicylamide of the formula

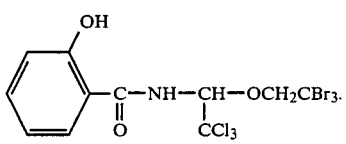

7. A fungicidal composition comprising a fungicidally effective amount of a compound according to claim 1 and a diluent.

* * * * *